(12) United States Patent
Matsue et al.

(10) Patent No.: US 10,620,146 B2
(45) Date of Patent: Apr. 14, 2020

(54) ELECTRODE CHIP

(71) Applicant: TOHOKU UNIVERSITY, Sendai-shi, Miyagi (JP)

(72) Inventors: Tomokazu Matsue, Sendai (JP); Kumi Inoue, Sendai (JP); Takahiro Ito, Sendai (JP); Hitoshi Shiku, Sendai (JP); Miho Ikegawa, Sendai (JP)

(73) Assignee: TOHOKU UNIVERSITY, Sendai-shi, Miyagi (JP)

( * ) Notice: Subject to any disclaimer, the term of this patent is extended or adjusted under 35 U.S.C. 154(b) by 0 days.

(21) Appl. No.: 16/131,396

(22) Filed: Sep. 14, 2018

(65) Prior Publication Data
US 2019/0017953 A1    Jan. 17, 2019

Related U.S. Application Data

(63) Continuation of application No. PCT/JP2017/004452, filed on Feb. 7, 2017.

(30) Foreign Application Priority Data

Mar. 18, 2016  (JP) .................................. 2016-055251

(51) Int. Cl.
| | | |
|---|---|---|
| G01N 27/403 | (2006.01) |
| G01N 27/27 | (2006.01) |
| G01N 27/30 | (2006.01) |
| G01N 27/49 | (2006.01) |
| G01N 27/42 | (2006.01) |
| G01N 27/48 | (2006.01) |
| G01N 33/00 | (2006.01) |

(52) U.S. Cl.
CPC ............. *G01N 27/27* (2013.01); *G01N 27/30* (2013.01); *G01N 27/403* (2013.01); *G01N 27/42* (2013.01); *G01N 27/48* (2013.01); *G01N 27/49* (2013.01); *G01N 33/0031* (2013.01)

(58) Field of Classification Search
CPC .... G01N 27/30; G01N 27/327; G01N 27/333; G01N 27/403
See application file for complete search history.

(56) References Cited

FOREIGN PATENT DOCUMENTS

JP     2005530179 A    10/2005

OTHER PUBLICATIONS

Online Cambridge Dictionary definition of "tip" as a noun. Downloaded Oct. 9, 2019; one page. (Year: 2019).*
Sep. 18, 2018, International Preliminary Report on Patentability issued in the International Patent Application No. PCT/JP2017/004452.
Apr. 11, 2017, International Search Report issued in the International Patent Application No. PCT/JP2017/004452.

(Continued)

*Primary Examiner* — Alexander S Noguerola
(74) *Attorney, Agent, or Firm* — Kenja IP Law PC

(57) ABSTRACT

An electrode chip including one auxiliary cell and a plurality of measurement cells on a substrate, where the auxiliary cell includes a reference electrode, a counter electrode, and an auxiliary cell-side working electrode, the measurement cell includes a driving electrode and a measurement cell-side working electrode, and the auxiliary cell-side working electrode and the measurement cell-side working electrode are electrically connected.

20 Claims, 15 Drawing Sheets

(56) References Cited

OTHER PUBLICATIONS

Kumi Inoue et al., A Study of Liquid Junction-Free Substitutional Stripping Voltammetry Method Using a Closed Bipolar Electrode System, Review of Polarography, 2015, p. 234, vol. 61, No. 3.

Kumi Y. Inoue et al., A Study for Amperometric Measurement Using a Closed Bipolar Electrode Systems, Chemical Sensors, 2015, pp. 49-51, vol. 31, Supplement B.

Kumi Y. Inoue et al., Development of Multi-Point Amperometric Detection Method That Requires No Reference Electrode Liquid Junction and Uses a Closed Bipolar Electrode System, The 62nd Annual Meeting of the Polarographic Society of Japan Koen Yoshishu, Laid-open: Nov. 1, 2016, p. 57.

Shinichiro Takano et al., Liquid-junction-free system for substitutional stripping voltammetry using a closed bipolar electrode system, Electrochemistry Communications, Feb. 27, 2016, pp. 34-37, vol. 66.

Stephen E. Fosdick et al., Bipolar Electrochemistry, Angewandte Chemie International Edition, 2013, pp. 10438-10456, vol. 52, Issue 40.

\* cited by examiner

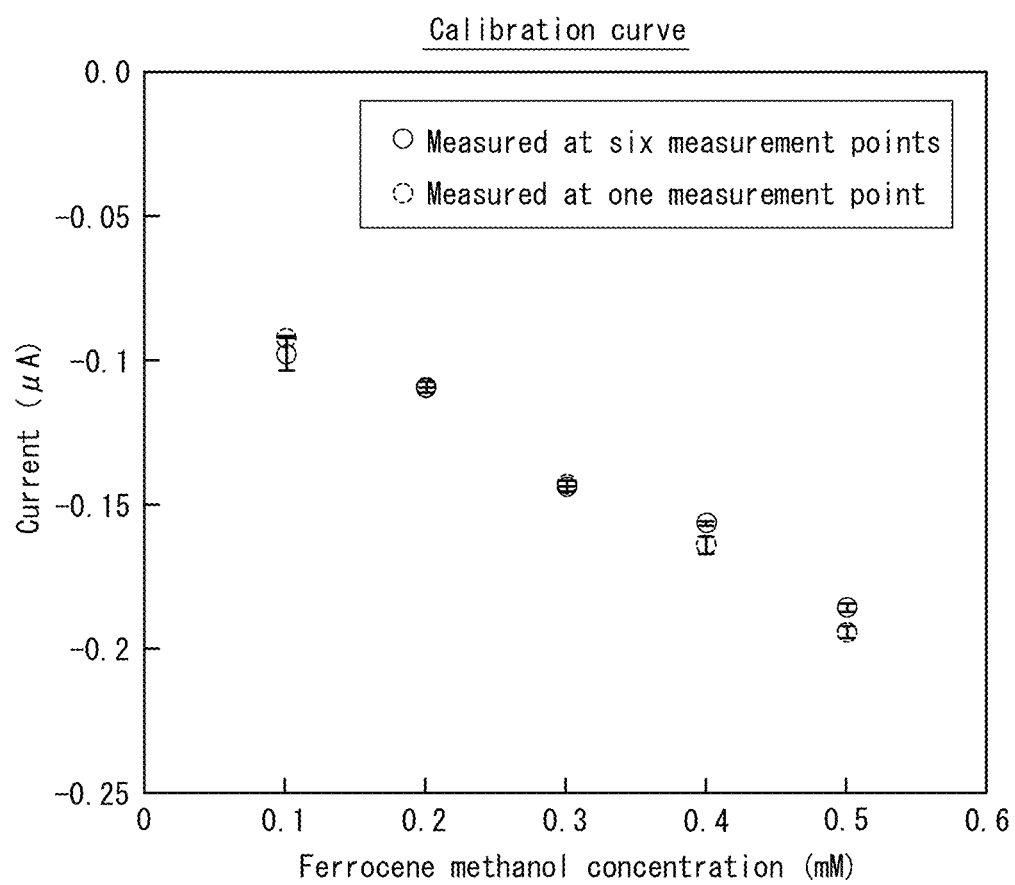

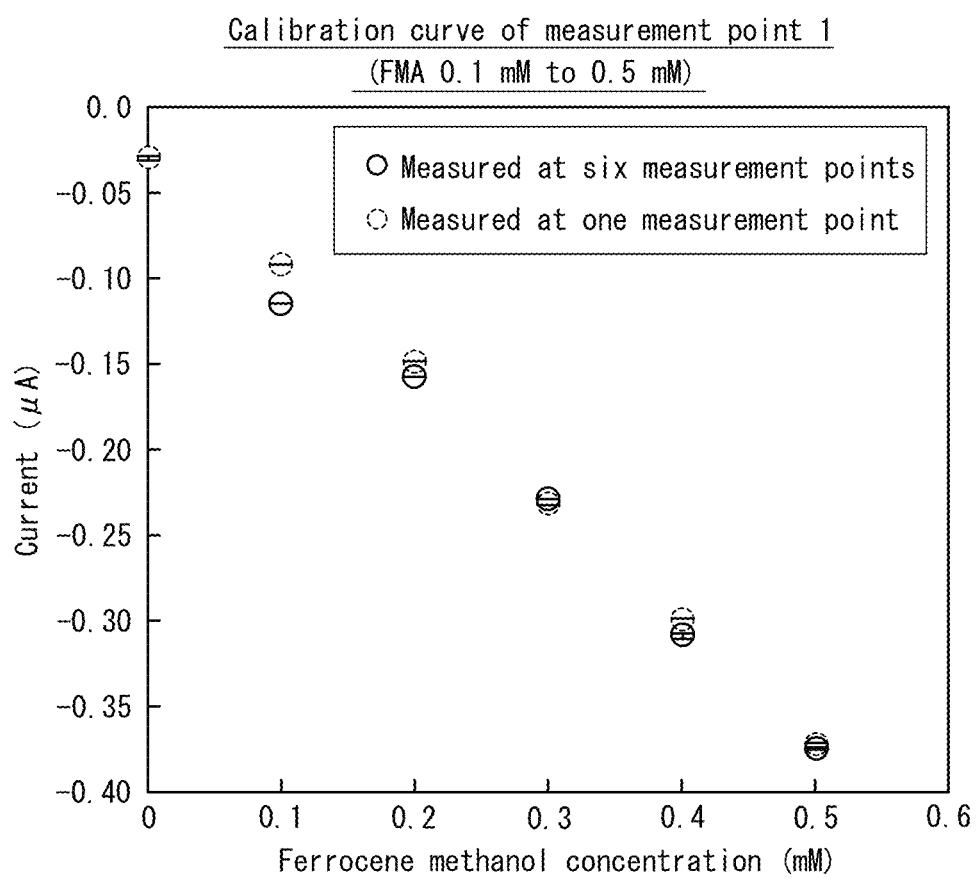

ELECTRODE CHIP

TECHNICAL FIELD

This disclosure relates to an electrode chip that can perform multiple measurements accurately with only one reference electrode.

BACKGROUND

Bipolar electrochemistry is a field dealing with phenomena where an electric conductor functions as a bipolar electrode when being immersed in a solution to which a voltage is applied. Various applications of the bipolar electrode have been reported since around 2000 such as electrochemical devices and electrode chips (see S. E. Fosdick, K. N. Knust, K. Scida, R. M. Cooks, Angew. Chem. Int. Ed. 52, 10438 (2013) (NPL 1)).

We have been developing a closed bipolarelectrode system (also referred to as "cBPES") in which a driving electrode and a potentiostat are used instead of a salt bridge and a liquid junction that electrically connect a measurement cell and an auxiliary cell in a regular conversion stripping method (see Chemical Sensors, Vol. 31 Supplement B (2015) (NPL 2), and Shinichiro Takano, Kumi Y. Inoue, Miho Ikegawa, Yasufumi Takahashi, Kosuke Ino, Hitoshi Shiku, Tomokazu Matsue (2016) Electrochemistry Communications in press (NPL 3)). This system can solve the problems of the conventional method such as salt precipitation and clogging in the salt bridge and liquid junction.

CITATION LIST

Non-Patent Literature

NPL 1: S. E. Fosdick, K. N. Knust, K. Scida, R. M. Cooks, Angew. Chem. Int. Ed. 52, 10438 (2013)
NPL 2: Chemical Sensors, Vol. 31 Supplement B (2015)
NPL 3: Shinichiro Takano, Kumi Y. Inoue, Miho Ikegawa, Yasufumi Takahashi, Kosuke Ino, Hitoshi Shiku, Tomokazu Matsue (2016) Electrochemistry Communications in press

SUMMARY

Technical Problem

However, the aforementioned prior art requires the prepared electrode chip have one measurement cell corresponding to one auxiliary cell, rendering it difficult to perform electrochemical measurements for a large number of samples in a short time.

Furthermore, an electrode chip according to the prior art still has room for improvement in the accuracy of electrochemical measurements.

It could thus be helpful to provide an electrode chip that can perform multiple measurements accurately with only one reference electrode.

Solution to Problem

We provide the following.

An electrode chip of this disclosure is an electrode chip including one auxiliary cell and a plurality of measurement cells on a substrate, where the auxiliary cell includes a reference electrode, a counter electrode, and an auxiliary cell-side working electrode, the measurement cell includes a driving electrode and a measurement cell-side working electrode, and the auxiliary cell-side working electrode and the measurement cell-side working electrode are electrically connected.

In the electrode chip of this disclosure, it is preferable that the measurement cell-side working electrode is surrounded by the driving electrode in the measurement cell.

In the electrode chip of this disclosure, it is preferable that the surface area of the auxiliary cell-side working electrode is larger than surface areas of a plurality of the measurement cell-side working electrodes.

In the electrode chip of this disclosure, it is preferable that the surface area of the auxiliary cell-side working electrode is larger than the surface area of any one of the measurement cell-side working electrodes.

In the electrode chip of this disclosure, it is preferable that the surface area of one of the driving electrodes is larger than the surface area of one of the measurement cell-side working electrodes.

In the electrode chip of this disclosure, it is preferable that the surface area of the counter electrode is larger than the surface area of the auxiliary cell-side working electrode.

In the electrode chip of this disclosure, it is preferable that a ratio of the surface area of the driving electrode to the surface area of the measurement cell-side working electrode is 2000% to 8000%.

In the electrode chip of this disclosure, it is preferable that the measurement cell further includes a measurement solution containing a detection substance, the auxiliary cell further includes an auxiliary solution containing an oxidation-reduction substance, and a ratio of the concentration of the detection substance in the measurement solution to the concentration of the oxidation-reduction substance in the auxiliary solution is 20% or less.

In the electrode chip of this disclosure, it is preferable that the counter electrode and the reference electrode are electrically insulated and independently provided in the auxiliary cell.

Advantageous Effect

According to this disclosure, it is possible to provide an electrode chip that can perform multiple measurements accurately with only one reference electrode.

BRIEF DESCRIPTION OF THE DRAWINGS

In the accompanying drawings:

FIG. 6 is a graph plotting the average current value (A) of the chronoamperogram (22 seconds to 25 seconds) against the ferrocene methanol concentration (mM) for the electrode chip of Example 1;

FIG. 12 is a graph plotting the average current value (A) of the chronoamperogram (22 seconds to 25 seconds) against the ferrocene methanol concentration (mM) for the electrode chip of Example 3;

DETAILED DESCRIPTION

The following describes an embodiment of the electrode chip of this disclosure in detail with reference to the drawings.

Figure 1A:
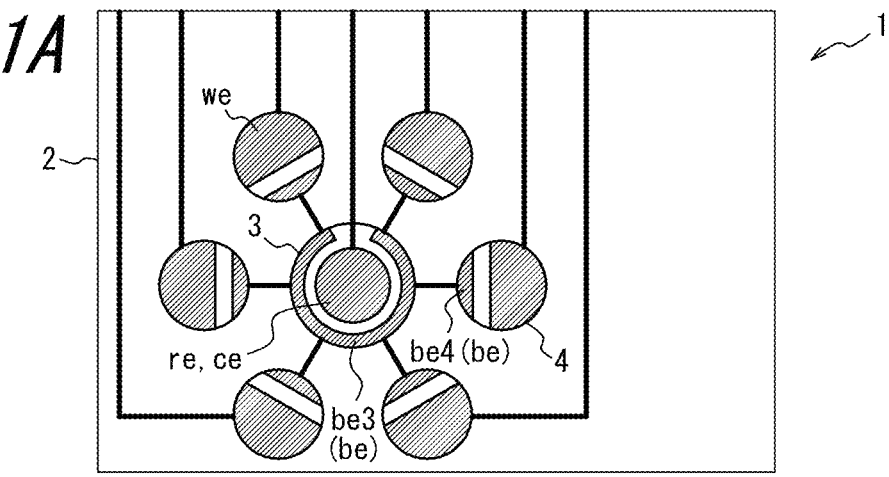
FIGS. 1A, 1B and 1C illustrate an electrode chip of the present embodiment, with FIG. 1A illustrating a top view of an example of the electrode chip of the present embodiment, FIG. 1B illustrating a top view of another example of the electrode chip of the present embodiment, and FIG. 1C illustrating a top view of a further example of the electrode chip of the present embodiment.
Figure 1B:
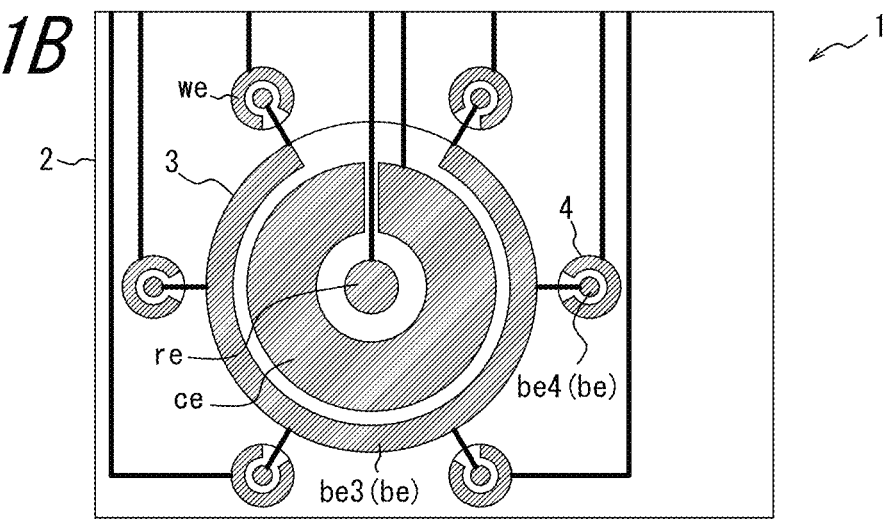
Figure 1C:
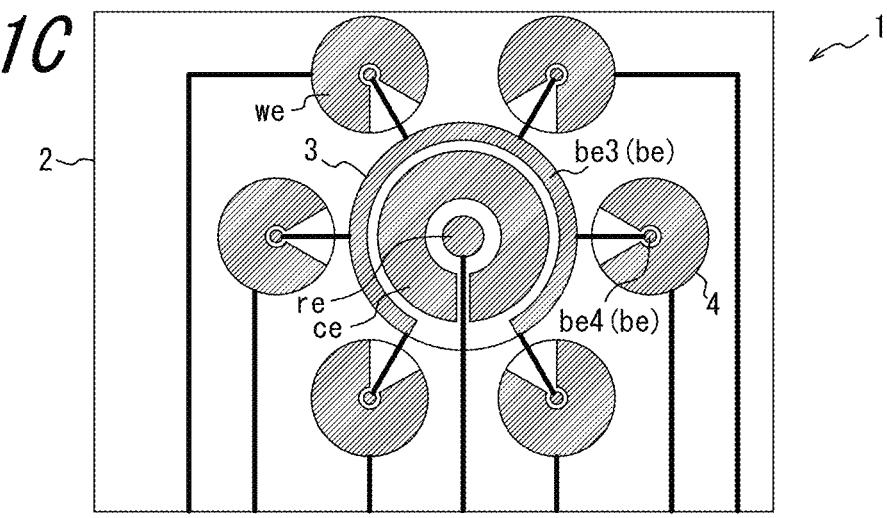

FIGS. 1A, 1B and 1C illustrate an electrode chip of the present embodiment, with FIG. 1A illustrating a top view of an example of the electrode chip of the present embodiment, FIG. 1B illustrating a top view of another example of the electrode chip of the present embodiment, and FIG. 1C illustrating a top view of a further example of the electrode chip of the present embodiment.

(Electrode Chip)

As illustrated in FIGS. 1A, 1B and 1C, the electrode chip 1 of the embodiment of this disclosure (hereinafter also referred to as "electrode chip 1") is provided with one auxiliary cell 3 and a plurality of measurement cells 4 on a substrate 2. In the electrode chip 1, the auxiliary cell 3 includes a reference electrode re, a counter electrode ce and an auxiliary cell-side working electrode be3, and the measurement cell 4 includes a driving electrode we and a measurement cell-side working electrode be4. FIGS. 1A, 1B and 1C do not illustrate the side view of the cells.

The auxiliary cell-side working electrode be3 and the measurement cell-side working electrode be4 are electrically connected to form a bipolar electrode be that electrically connects the two cells 3 and 4.

The auxiliary cell-side working electrode be3 may be referred to as an auxiliary electrode, and the measurement cell-side working electrode be4 may be referred to as a detection electrode.

Figure 2:
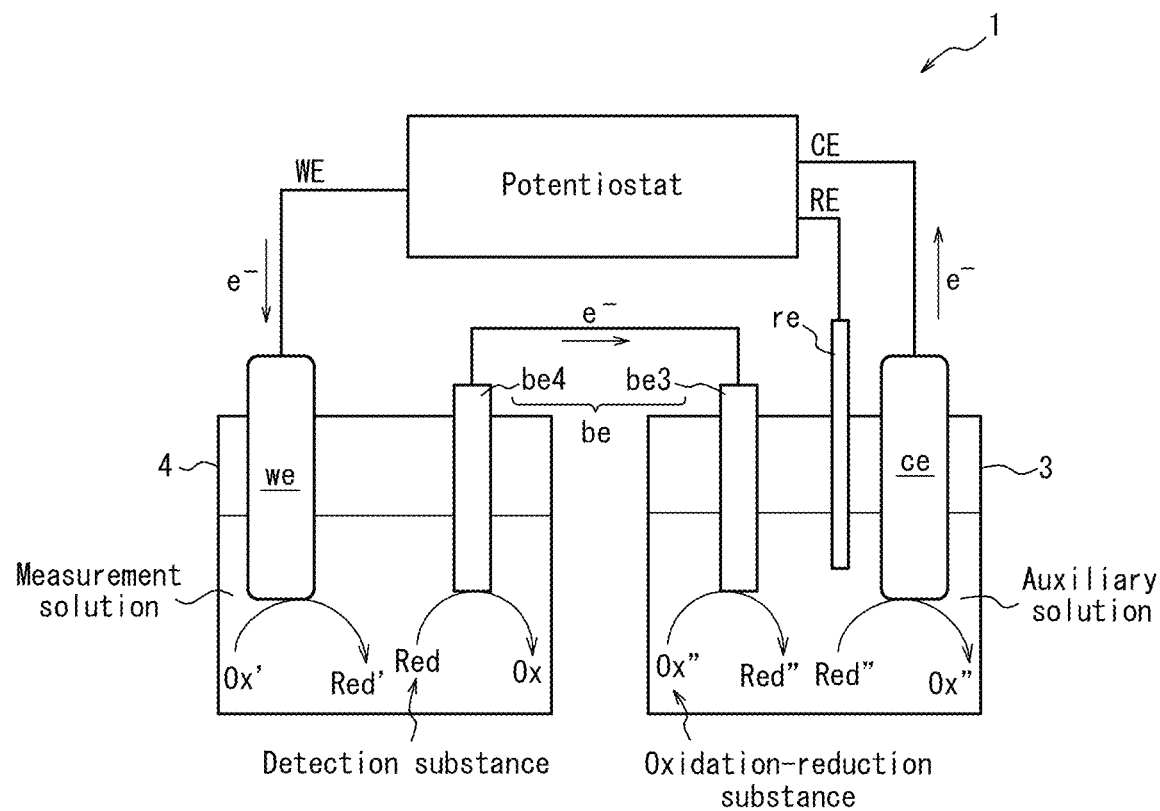
FIG. 2 schematically illustrates the principle of an electrochemical measurement performed with the electrode chip of the embodiment of this disclosure.

FIG. 2 schematically illustrates the principle of an electrochemical measurement performed with the electrode chip 1 of the embodiment of this disclosure.

In the electrode chip 1, the auxiliary cell 3 is added with an auxiliary solution (as described later) containing an oxidation-reduction substance, and the measurement cell 4 is added with a measurement solution (as described later) containing a detection substance. Furthermore, the driving electrode we, the counter electrode ce and the reference electrode re of the electrode chip 1 are connected to a working electrode WE terminal, a counter electrode CE terminal and a reference electrode RE terminal of a potentiostat respectively. A predetermined electric potential is applied between the driving electrode we and the reference electrode re using the potentiostat.

Then, in the measurement cell 4 of the electrode chip 1, an oxidation reaction of the detection substance occurs on the measurement cell-side working electrode be4 while a reverse reduction reaction occurs on the driving electrode we; on the other hand, in the auxiliary cell 3 of the electrode chip 1, a reduction reaction of the oxidation-reduction substance contained in the auxiliary solution occurs on the auxiliary cell-side working electrode be3 while a reverse oxidation reaction occurs on the counter electrode ce (see FIG. 2).

As described above, the reference electrode re is arranged in the auxiliary cell 3, which is a different cell from the measurement cell 4 containing the detection substance. When a reduction reaction occurs on the driving electrode we, the reaction of the detection substance occurring on the measurement cell-side working electrode be4 is an oxidation reaction.

It is important for the electrode chip 1 to take the oxidation reaction on the measurement cell-side working electrode be4 as the rate-determining reaction of the entire chip 1 and to form a calibration curve with the concentration of the detection substance and the measured current value, by which a concentration-dependent measurement of the detection substance can be performed.

As described above, an oxidation reaction of the detection substance contained in the measurement solution occurs on the measurement cell-side working electrode be4, and a reduction reaction of the oxidation-reduction substance contained in the auxiliary solution occurs on the auxiliary cell-side working electrode be3 in the electrode chip 1 as illustrated in FIG. 2, yet the electrode chip of this disclosure is not limited to this example. It is acceptable that a reduction reaction of the detection substance contained in the measurement solution occurs on the measurement cell-side working electrode be4, and an oxidation reaction of the oxidation-reduction substance contained in the auxiliary solution occurs on the auxiliary cell-side working electrode be3.

In order to obtain a cyclic voltammetry measurement chart similar to that of a regular three-electrode system and to set a voltage applied during an amperometric measurement similar to that of a regular three-electrode system, the reference electrode re conventionally is arranged in the same cell as the one containing the detection substance.

There is a possibility that the reference electrode re may leak or elute the components constituting the reference electrode re ($Ag^+$ or $Cl^-$ in a case of Ag/AgCl) into the cell.

The electrode chip 1 of the present embodiment arranges the reference electrode re in the auxiliary cell 3, which is a different cell from the measurement cell 4 containing the detection substance, and therefore the detection substance and the reference electrode re have no contact to each other. In the electrode chip 1 of the present embodiment, the detection substance and the components constituting the reference electrode re do not mix with each other, thereby improving the measurement accuracy of the detection substance.

The electrode chip 1 of the present embodiment arranges the reference electrode re in the auxiliary cell 3, which is a different cell from the measurement cell 4 containing the detection substance. In this way, it is possible to perform a plurality of electrochemical measurements (multiple measurements) with one reference electrode re (and one counter electrode ce) without switching the connection of the terminals or reconnecting the terminals.

Furthermore, the electrode chip 1 of the present embodiment has less wiring as compared with a case of using a plurality of three-electrode systems that include one driving electrode we, one reference electrode re and one counter electrode ce, and provides more space for arranging members on the substrate 2. Therefore, it is possible to miniaturize the size of the electrode chip 1.

Because the electrode chip 1 of the present embodiment takes the oxidation reaction on the measurement cell-side working electrode be4 (or the reduction reaction on the measurement cell-side working electrode be4) as the rate-determining reaction of the entire chip 1, the electrode chip 1 preferably possesses the following features with respect to the surface area of each electrode.

In the electrode chip 1, it is preferable that the surface area of the auxiliary cell-side working electrode be3 is larger than a plurality of the measurement cell-side working electrodes be4 (feature a1). With such a configuration, it is possible to perform electrochemical measurements suitably even when the measurements are carried out simultaneously in a plurality of the measurement cells using a multi-channel potentiostat.

Additionally, in the electrode chip 1, it is preferable that the surface area of the auxiliary cell-side working electrode be3 is larger than the surface area of any one of the measurement cell-side working electrodes be4, in other words, it is preferable that the auxiliary cell-side working electrode be3 has a larger surface area than the measurement cell-side working electrode be4 that has the largest surface area among the measurement cell-side working electrodes be4 (feature a2). With such a configuration, it is possible to perform electrochemical measurements suitably even when the measurements are carried out sequentially in one measurement cell by switching or other methods using a single-channel potentiostat.

It is more preferable that the electrode chip 1 possesses both the features a1 and a2.

Note that the surface area here may be the area in a plan view when each electrode has a determined thickness.

Furthermore, in the electrode chip 1, it is preferable that the surface area of one driving electrode we is larger than the surface area of one measurement cell-side working electrode be4 (feature b).

Moreover, in the electrode chip 1, it is preferable that the surface area of the counter electrode ce is larger than the surface area of the auxiliary cell-side working electrode be3 (feature c).

In order to explain the features of the present embodiment more specifically, the following describes an example, another example, and a further example of the electrode chip 1 of the present embodiment in detail.

FIG. 1A illustrates a top view of an example of the electrode chip 1 of the present embodiment. The same elements as those of the electrode chip 1 of the present embodiment have the same reference signs below, and the description thereof is omitted.

An example of the electrode chip 1 of the present embodiment is an electrode chip including one auxiliary cell 3 and six measurement cells 4 on a substrate 2.

In this example, a driving electrode we and a measurement cell-side working electrode be4 are provided in the measurement cell 4 so that the edges indicating their ends are opposed to each other (see the rectangular frame in FIG. 1A).

As illustrated in FIG. 1A, one electrode may function as the counter electrode ce and the reference electrode re simultaneously in this example.

With this example of the electrode chip 1 of the present embodiment, it is possible to obtain the effect of the electrode chip 1 of the present embodiment as described above.

FIG. 1B illustrates a top view of another example of the electrode chip 1 of the present embodiment. The same elements as those of the electrode chip 1 of the present embodiment have the same reference signs below, and the description thereof is omitted.

The overall structure of the other example of the electrode chip 1 of the present embodiment is the same as that of the above-described example of the electrode chip 1. However, in the other example of the electrode chip 1, the measurement cell-side working electrode be4 is surrounded by the driving electrode we in the measurement cell 4, and the counter electrode ce and the reference electrode re are electrically insulated and independently provided.

With the configuration of the other example of the electrode chip 1 of the present embodiment where the measurement cell-side working electrode be4 is surrounded by the driving electrode we, it is easy to ensure that, when adding a measurement solution to the measurement cell 4, the entire driving electrode we is in contact with the measurement solution, thereby enhancing the reproducibility of electrochemical measurements.

When producing the electrode chip 1, it usually forms the electrodes we, ce and re and the wiring on the substrate 2 first and then arranges the cells 3 and 4 on the substrate 2. In this way, it is easy to, when determining the region of the cells 3 and 4, set the entire measurement cell-side working electrode be4 within the region, which enhances the reproducibility during the preparation of the measurement cell-side working electrode be4. As a result, the reproducibility of electrochemical measurements can be enhanced.

More specifically, in the other example, the measurement cell 4 has a circular shape in a plan view, the measurement cell-side working electrode be4 has a circular shape in a plan view and is located at the center of the measurement cell 4, and the driving electrode we has a "U" shape in a plan view and is located at the periphery of the measurement cell 4.

FIG. 1C illustrates a top view of a further example of the electrode chip 1 of the present embodiment. The same elements as those of the electrode chip 1 of the present embodiment have the same reference signs below, and the description thereof is omitted.

The overall structure of the further example of the electrode chip 1 of the present embodiment is the same as that of the above-described other example of the electrode chip 1. However, in the measurement cell 4 of the further example of the electrode chip 1, the surface area of the driving electrode we is larger than the surface area of the measurement cell-side working electrode be4.

With the configuration of the further example of the electrode chip 1 of the present embodiment, it is easy to take the oxidation-reduction reaction on the measurement cell-side working electrode be4 rather than the oxidation-reduction reaction on the driving electrode we as the rate-determining reaction of the entire chip 1 as described above. In this way, it is possible to obtain a calibration curve using the concentration of the detection substance and the measured current value, and to perform a concentration-dependent measurement of the detection substance.

Note that the surface area here may be the area in a plan view when each electrode has a determined thickness.

More specifically, in the further example, the ratio of the surface area of the driving electrode we to the surface area of the measurement cell-side working electrode be4 in one measurement cell 4 is preferably 1000% to 50000%, and more preferably 2000% to 8000%.

As illustrated in FIGS. 1A to 1C, in the above-described example, other example and further example of the electrode chip 1 of the present embodiment, the reference electrode re and the counter electrode ce are surrounded by the auxiliary cell-side working electrode be3 in the auxiliary cell 3. More specifically, in the auxiliary cell 3, the auxiliary cell-side working electrode be3 is located at the periphery of the auxiliary cell 3, and the reference electrode re and the counter electrode ce are located at the center of the auxiliary cell 3.

With such a configuration, it is easy to ensure that, when adding an auxiliary solution to the auxiliary cell 3, both the counter electrode ce and the auxiliary cell-side working electrode be3 are in contact with the auxiliary solution, thereby enhancing the reproducibility of electrochemical measurements.

The following describes each element of the electrode chip 1 of the present embodiment in detail.

—Substrate—

The material of the substrate 2 is not particularly limited and may be appropriately determined depending on the purpose and use. Examples of the material of the substrate 2 include glass, resin, and ceramic, among which an insulating material is preferable.

These materials may be used alone or in combination of two or more.

—Driving Electrode, Counter Electrode, and Working Electrode—

Examples of the material of the driving electrode we, counter electrode ce, and working electrode re include a carbon material, a metal, a conductive polymer material, and a semiconductor.

Examples of the carbon material include glassy carbon, carbon paste, graphite, and diamondlike carbon. Examples of the metal include gold, platinum, palladium, and silver. Examples of the conductive polymer material include polyethylenedioxythiophene, polyacetylene, and polypyrrole.

These materials may be used alone or in combination of two or more.

—Reference Electrode—

The material of the reference electrode re is not particularly limited and may be appropriately determined depending on the purpose and use. Examples of the material of the reference electrode re include Ag/AgCl, which is usually used in electrochemical measurements.

The material of the wiring between the electrodes is not particularly limited and may be the same as the material of the driving electrode we, counter electrode ce, and working electrode be as described above.

The material of each of the measurement cell 4 and the auxiliary cell 3 is not particularly limited and may be appropriately determined depending on the purpose and use. The bottom face of the cell may be the substrate on which the electrodes and the wiring are arranged, and the side face of the cell may be, for example, a resin.

The area of the bottom face, the height of the side face and other characteristics of the cell are not particularly limited.

When performing an electrochemical measurement using the electrode chip 1 of the present embodiment, a measurement solution, which is an aqueous solution containing a detection substance and optionally a supporting salt or a buffering agent, is added to the measurement cell 4, and an auxiliary solution, which is an aqueous solution containing an oxidation-reduction substance and optionally a supporting salt or a buffering agent, is added to the auxiliary cell 3. Additionally, the working electrode terminal (WE) of the potentiostat is connected to the driving electrode we, the counter electrode CE terminal of the potentiostat is connected to the counter electrode ce, and the reference electrode RE terminal of the potentiostat is connected to the reference electrode re.

It is desirable that the auxiliary solution here contains a reversible oxidation-reduction substance and sufficient supporting salt.

The shape of the electrode chip 1 of the present embodiment in a plan view is not particularly limited and may be appropriately determined depending on the purpose and use. The shape of the electrode chip 1 may be, for example, rectangular, square, elliptical, or circular.

The dimension of the electrode chip 1 of the present embodiment is not particularly limited, and may be 20 mm to 120 mm in length, 20 mm to 120 mm in width, and 0.3 mm to 5 mm in thickness.

The following describes the substances used in an electrochemical measurement performed with the electrode chip 1 of the present embodiment in detail.

—Detection Substance—

The detection substance in the measurement solution is not particularly limited as long as it is a substance serving as the substrate of an oxidation-reduction reaction. The detection substance may be a substance that causes an oxidation-reduction reaction by itself, or may be a substance that causes an oxidation-reduction reaction in the presence of a catalyst or a co-catalyst of an enzyme or a coenzyme (such as an electron transfer mediator).

Examples of the detection substance include ferrocene methanol, p-aminophenol, p-nitroaniline, p-methoxyaniline ruthenium hexamine, potassium ferrocyanide, potassium ferricyanide, ferrocenecarboxylic acid; and glucose in the presence of glucose oxidase and electron transfer mediator (such as ferrocene methanol).

These substances may be used alone or in combination of two or more.

—Oxidation-Reduction Substance—

The oxidation-reduction substance used in the auxiliary solution is not particularly limited as long as it is a substance serving as the substrate of an oxidation-reduction reaction. The oxidation-reduction substance may be the same as or different from the aforementioned examples of the detection substance.

The oxidation-reduction substance in the auxiliary solution is preferably in a state where about half of the oxidation-reduction substance is oxidant and the other half is reductant. For example, the oxidation-reduction substance may contain 2.5 mM of potassium ferrocyanide and 2.5 mM of potassium ferricyanide.

—Supporting Salt—

The supporting salt is used as an electrolyte in the measurement solution and the auxiliary solution, and may be, for example, a metal halide or a metal nitrate.

Examples of the metal halide include potassium chloride. Examples of the metal nitrate include $AgNO_3$ and $KNO_3$.

These substances may be used alone or in combination of two or more.

—Buffering Agent—

The buffering agent is used, for example, to adjust the pH of the measurement solution and the auxiliary solution. Examples of the buffering agent include Tris-acetate-EDTA, Tris-HCl, phosphoric acid, HEPES and PIPES, and these substances may be used as a buffer solution for preparing the measurement solution and the auxiliary solution.

These substances may be used alone or in combination of two or more.

From the perspective of taking the oxidation-reduction reaction on the measurement cell-side working electrode be4 as the rate-determining reaction of the entire chip, it is preferable that the concentration of the detection substance (or the electron transfer mediator whose concentration varies according to the concentration of the detection substance) in the measurement solution is sufficiently smaller than the concentration of the oxidation-reduction substance in the auxiliary solution during the measurement.

Specifically, the ratio of the concentration of the detection substance to the concentration of the oxidation-reduction substance (or the electron transfer mediator whose concentration varies according to the concentration of the detection substance) is preferably 30% or less. The ratio is more preferably 20% or less. The ratio is particularly preferably 10% or less.

More specifically, in a case where the detection substance in the measurement solution is paraaminophenol and the oxidation-reduction substance in the auxiliary solution is silver, for example, the ratio is preferably 30% or less and more preferably 20% or less.

The electrode chip 1 of the present embodiment can be produced with a known technique such as photolithography, etching, mask vapor deposition, screen printing, gravure printing, flexographic printing, or inkjet printing.

The electrode chip of this disclosure can be suitably used, for example, in an immunosensor or a urine sensor.

EXAMPLES

The following describes the present disclosure in more detail with reference to Examples. However, the present disclosure is not limited to the following Examples in any way.

A. Preparation of Electrode Chip

First, an electrode chip was designed using Vector Works (made by A&A).

Subsequently, photomasks to be used later were prepared. Specifically, the design was printed on an inkjet film (PF-10R-A4 made by SunHayato) using an inkjet printer.

Subsequently, electrodes were prepared by photolithography with the following processes (1) to (7).

(1) Preparation of substrate: a microscope slide was cut in half by a glass cutter, and the microscope slide was used as a substrate.

(2) Cleaning: the glass substrate was washed with a neutral detergent; subsequently, the glass substrate was laid in a staining dish and subjected to ultrasonic cleaning with acetone for 10 minutes and then with 2-propanol for 10 minutes; furthermore, the glass substrate was subjected to $O_2$ plasma ashing for 5 minutes to remove organic residues.

(3) Coating of photoresist: a spin coater was used to spin-coat OAP (containing hexamethyldisilazane) as a hydrophobizing agent on the glass substrate at 3000 rpm for 10 seconds, and then spin-coat S1818 (made by Shipley) as a positive photoresist on the glass substrate at 3000 rpm for 30 seconds. Subsequently, in order to remove the solvent of the photoresist, the glass substrate was prebaked on a hot plate at 65° C. for 1 minute, then 95° C. for 5 minutes, and then 65° C. for 3 minutes, and was allowed to naturally cool at room temperature.

(4) Exposure: the glass substrate was exposed to a mercury lamp for 14 seconds using the previously prepared photomask.

(5) Development: the glass substrate was immersed in an exclusive developing solution CD-26 DEVELOPER, which is an alkaline aqueous solution, for 6 minutes while spraying the developing solution on the pattern with a dropping pipette. In this way, the photosensitive part was eluted.

(6) Sputtering: the glass substrate was subjected to $O_2$ plasma ashing for 90 seconds to remove dirt on the surface; subsequently, the glass substrate was sputtered using a sputtering apparatus with 2 minutes of Ti, then 2 minutes of Pt, and then 8 minutes of Au, where the flow rate of Ar was 10 cm³/min, the pressure inside the chamber was 10 Pa, and the output of RF was 200 W.

(7) Lift-off: lift-off was performed by immersing the glass substrate in acetone and spraying the acetone with a dropping pipette so that metal other than the electrode portion was removed. In a case where the metal other than the electrode portion still remained, the glass substrate was rubbed with a swab or subjected to ultrasonic treatment until the metal was completely removed.

Subsequently, an insulating layer was prepared by photolithography with the following processes (1) to (5). Note that this step was performed in all Examples except Example 1 (as described later).

(1) Coating of photoresist: a spin coater was used to spin-coat SU-8 3005 (made by MICROCHEM) as a negative photoresist on the glass substrate, on which a first layer had been formed, at 3000 rpm for 30 seconds. Subsequently, in order to remove the solvent of the photoresist, the glass substrate was prebaked on a hot plate at 65° C. for 1 minute, then 95° C. for 5 minutes, and then 65° C. for 3 minutes, and then was allowed to naturally cool at room temperature.

(2) Exposure: the glass substrate was exposed to a mercury lamp for 400 counts using the previously prepared photomask, where the position of the mask was adjusted so that the alignment mark of the mask for the second layer was aligned with the alignment mark of the first layer.
(3) Post-baking: for the crosslinking reaction of the exposed part, the glass substrate was postbaked on a hot plate at 65° C. for 1 minute, then 95° C. for 5 minutes, and then 65° C. for 3 minutes, and then was allowed to naturally cool at room temperature.
(4) Development: the glass substrate was immersed in SU-8DEVELOPER and then sprayed with the developing solution by a dropping pipette for 3 minutes so that the nonphotosensitive part was eluted. Finally, the glass substrate was rinsed with isopropanol.
(5) Hard-baking: the glass substrate was hard-baked at 180° C. for 30 minutes. In this way, the solvent and moisture in the photoresist was removed, the residual photosensitizer was thermally crosslinked, and the adhesion with the first layer and the corrosion resistance were enhanced.

Finally, a water-repellent tape (blue) was affixed with the following processes (1) to (2) to prepare an insulating layer. Note that this tape functioned as a side surface of the auxiliary cell and the measurement cell in Examples 1 to 3 (as described later).
(1) An ELEGRIP tape (GD-60-23A) was cut by a cutting plotter into the design according to the design drawing made by Vector Works.
(2) The cut tape was affixed to the prepared substrate.

Figure 3A:
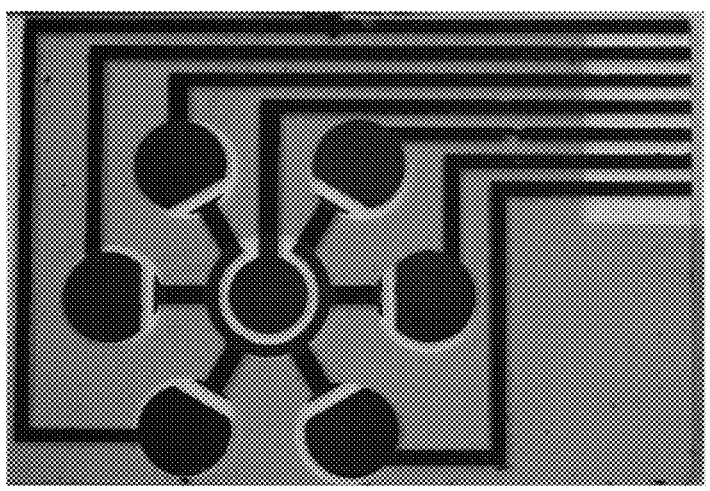
FIGS. 3A, 3B and 3C illustrate the electrode chips of Examples, with FIG. 3A illustrating a top view of the electrode of Example 1, FIG. 3B illustrating a top view of the electrode chip of Example 2, and FIG. 3C illustrating a top view of the electrode chip of Example 3.

An electrode chip (size: 76 mm×52 mm) having the structure as illustrated in FIG. 3A was prepared as the electrode chip of Example 1.

Figure 3B:
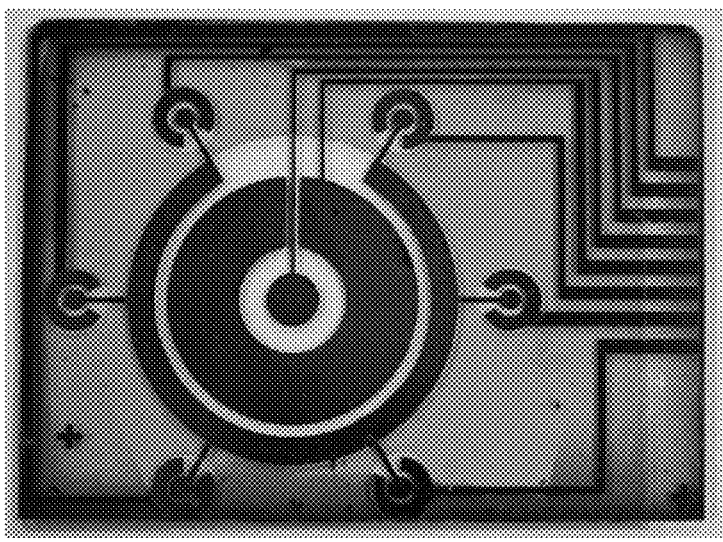

An electrode chip (size: 52 mm×38 mm) having the structure as illustrated in FIG. 3B was prepared as the electrode chip of Example 2.

Figure 3C:
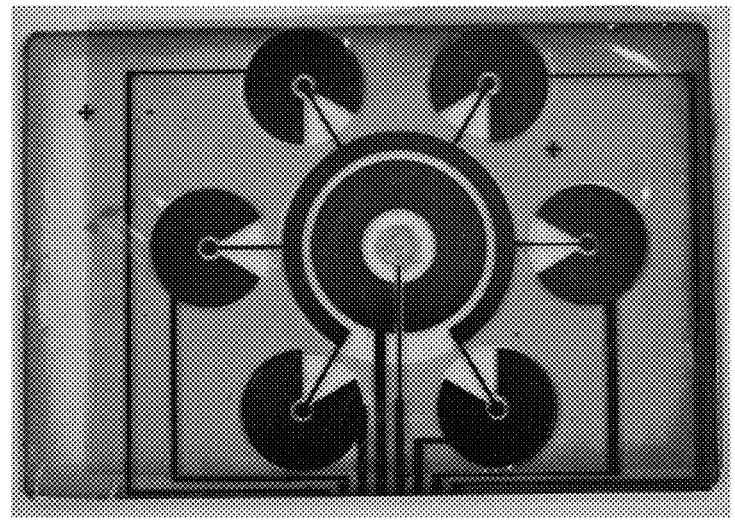

An electrode chip (size: 76 mm×52 mm) having the structure as illustrated in FIG. 3C was prepared as the electrode chip of Example 3.

The ratio of the surface area of the driving electrode to the surface area of the measurement cell-side working electrode in the measurement cell was 5132% in Example 1, 496% in Example 2, and 5284% in Example 3.

B. Cyclic Voltammetry Measurement and Chronoamperometry Measurement

The electrode chips of Examples 1 to 3 were used to perform electrochemical measurements with a potentiostat (product name: HA1010mM4, made by HOKUTO DENKO).

Ferrocene methanol (FMA) (made by Aldrich) was used as a detection substance in the measurement cell.

Potassium ferrocyanide (made by KANTO CHEMICAL) and potassium ferricyanide (made by KANTO CHEMICAL) were used as oxidation-reduction substances in the auxiliary cell.

KCl (made by Wako Pure Chemical Corporation) was used as a supporting salt, and HEPES (made by Wako Pure Chemical Corporation) was used as a buffering agent.

The counter electrode CE terminal of the potentiostat was connected to the counter electrode, and the reference electrode RE terminal of the potentiostat was connected to the reference electrode.

B-1. Electrode Chip of Example 1

An aqueous solution of 0 mM to 0.5 mM of FMA, 0.1 mM of HEPES and 0.1 mM of KCl was added to the first measurement cell of the electrode chip of Example 1. Nothing was added to the other second to sixth measurement cells. An aqueous solution of 2.5 mM of potassium ferrocyanide, 2.5 mM of potassium ferricyanide, 0.1 mM of HEPES, and 3 M of KCl was added to the auxiliary cell. The working electrode WE terminal of the potentiostat was connected to the first measurement cell, and the second to sixth measurement cells were left open.

Cyclic voltammetry measurements were performed under the following conditions: sweep rate: 20 mV/s, electric potential: 0.365 V→−0.1 V (−0.2 V)→0.5 V→0.365 V, and FMA concentration: 0 mM to 0.5 mM.

Chronoamperometry measurements were performed under the following conditions: applied voltage: −0.05 V, application time: 30 s, and FMA concentration: 0 mM to 0.5 mM.

Figure 4A:
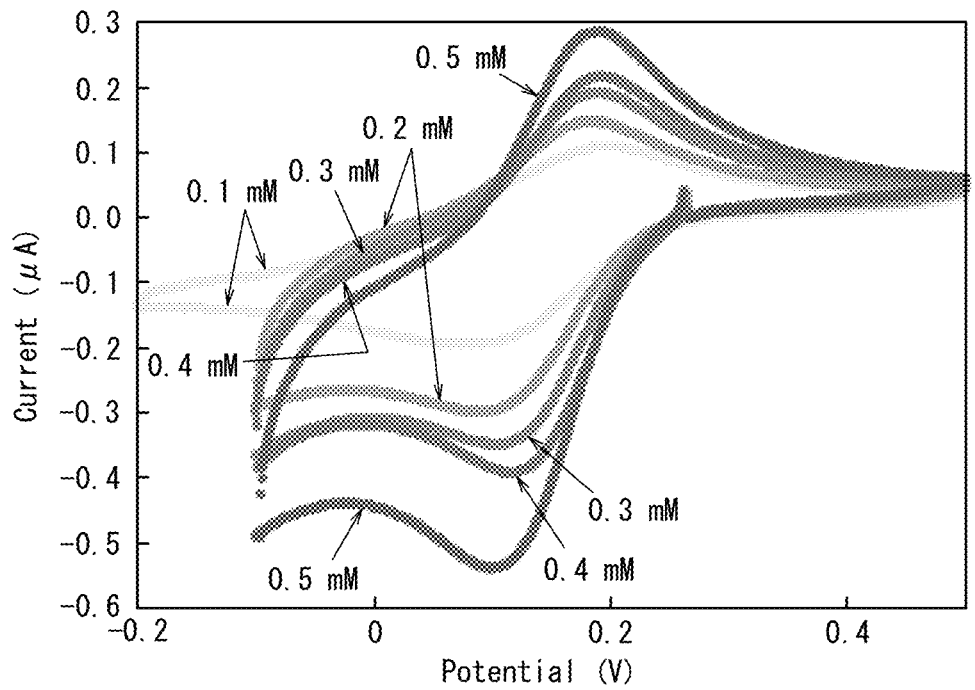
FIGS. 4A and 4B illustrate the evaluation results of the electrochemical measurements performed with the first measurement cell of the electrode chip of Example 1, with FIG. 4A illustrating the results of the cyclic voltammetry measurements, and FIG. 4B illustrating the results of the chronoamperometry measurements.
Figure 4B:
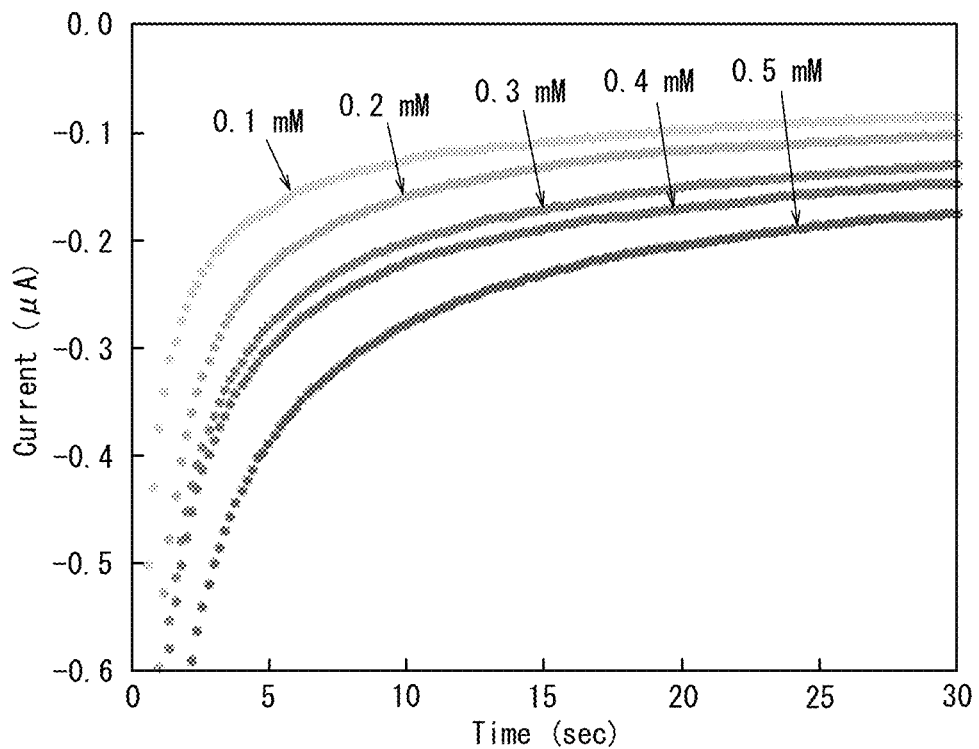

FIGS. 4A and 4B illustrate the evaluation results of the electrochemical measurements performed with the first measurement cell of the electrode chip of Example 1, with FIG. 4A illustrating the results of the cyclic voltammetry measurements, and FIG. 4B illustrating the results of the chronoamperometry measurements.

An aqueous solution of 0 mM to 0.5 mM of FMA, 0.1 mM of HEPES, and 0.1 mM of KCl was added to the first to sixth measurement cells of the electrode chip of Example 1. An aqueous solution of 0.5 mM of FMA was added to the other second to sixth measurement cells. An aqueous solution of 2.5 mM of potassium ferrocyanide, 2.5 mM of potassium ferricyanide, 0.1 mM of HEPES, and 3 M of KCl was added to the auxiliary cell. The working electrode WE terminal of the potentiostat was sequentially connected to the first to sixth measurement cells.

Cyclic voltammetry measurements were performed under the following conditions: sweep rate: 20 mV/s, electric potential: 0.365 V→−0.1 V (−0.2 V)→0.5 V→0.365 V, and FMA concentration: 0 mM to 0.5 mM.

Chronoamperometry measurements were performed under the following conditions: applied voltage: −0.05 V, application time: 30 s, and FMA concentration: 0 mM to 0.5 mM.

Figure 5A:
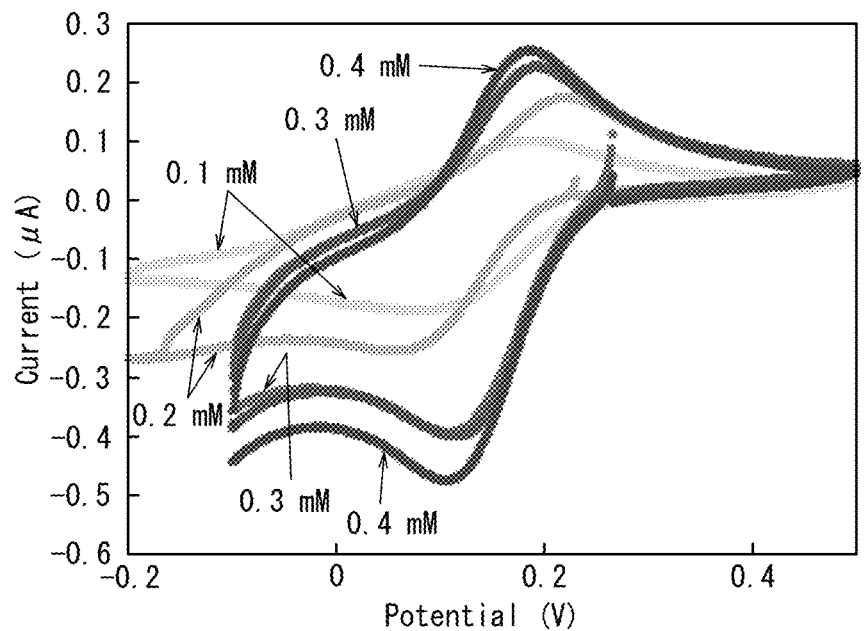
FIGS. 5A and 5B illustrate the evaluation results of the electrochemical measurements performed with the first to sixth measurement cells of the electrode chip of Example 1, with FIG. 5A illustrating the results of the cyclic voltammetry measurements, and FIG. 5B illustrating the results of the chronoamperometry measurements.
Figure 5B:
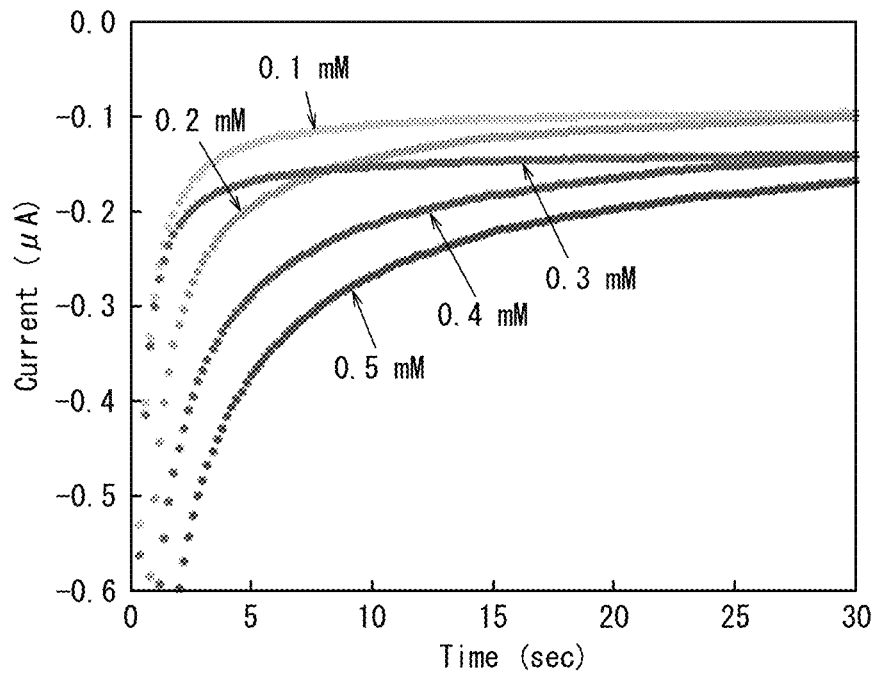

FIGS. 5A and 5B illustrate the evaluation results of the electrochemical measurements performed with the first to sixth measurement cells of the electrode chip of Example 1, with FIG. 5A illustrating the results of the cyclic voltammetry measurements, and FIG. 5B illustrating the results of the chronoamperometry measurements.

FIG. 6 is a graph plotting the average current value (A) of the chronoamperogram (22 seconds to 25 seconds) against the ferrocene methanol concentration (mM) for the electrode chip of Example 1.

It is understood from the result illustrated in FIG. 6 that the electrode chip can perform electrochemical measurements suitably in both cases of single channel and multi-channel.

B-2. Electrode Chip of Example 2

An aqueous solution of 0 mM to 0.5 mM of FMA, 0.1 mM of HEPES, and 0.1 mM of KCl was added to the first measurement cell of the electrode chip of Example 2. Nothing was added to the other second to sixth measurement cells. An aqueous solution of 2.5 mM of potassium ferrocyanide, 2.5 mM of potassium ferricyanide, 0.1 mM of HEPES, and 3 M of KCl was added to the auxiliary cell. The working electrode WE terminal of the potentiostat was connected to the first measurement cell, and the second to sixth measurement cells were left open.

Cyclic voltammetry measurements were performed under the following conditions: sweep rate: 20 mV/s, electric potential: 0.365 V→−0.4 V→0.5 V→0.365 V, and FMA concentration: 0 mM to 0.5 mM.

Figure 7A:
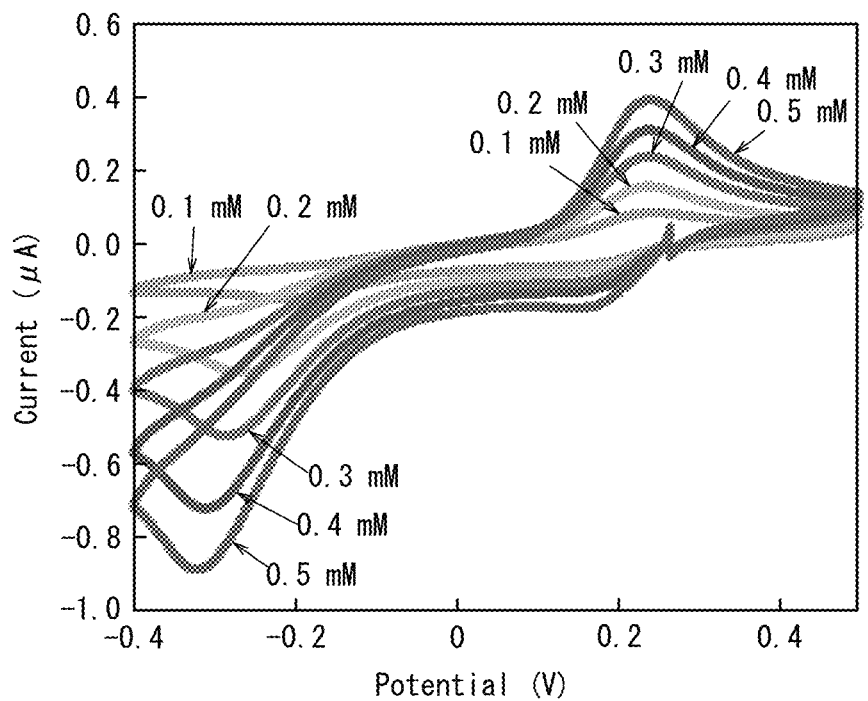
FIG. 7A illustrates the results of the cyclic voltammetry measurements performed with the first measurement cell of the electrode chip of Example 2.

FIG. 7A illustrates the results of the cyclic voltammetry measurements performed with the first measurement cell of the electrode chip of Example 2.

It was confirmed from the results illustrated in FIG. 7A that the peak appearance caused by FMA oxidation is quite different from each other at low potentials. The reason may be the relatively small surface area of the driving electrode.

An aqueous solution of 0 mM to 0.5 mM of FMA, 0.1 mM of HEPES and 0.1 mM of KCl was added to the first measurement cell of the electrode chip of Example 2. An aqueous solution of 0.5 mM of FMA was added to the other second to sixth measurement cells. An aqueous solution of 2.5 mM of potassium ferrocyanide, 2.5 mM of potassium ferricyanide, 0.1 mM of HEPES, and 3 M of KCl was added to the auxiliary cell. The working electrode WE terminal of the potentiostat was connected to the first measurement cell, and the second to sixth measurement cells were left open.

Cyclic voltammetry measurements were performed under the following conditions: sweep rate: 20 mV/s, electric potential: 0.365 V→−0.4 V→0.5 V→0.365 V, and FMA concentration: 0 mM to 0.5 mM.

Figure 7B:
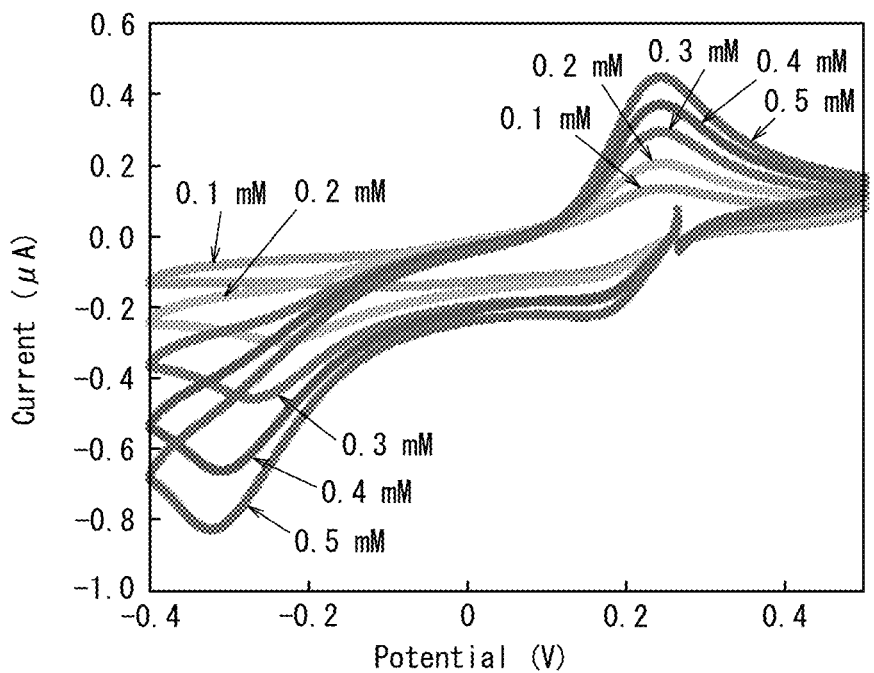
FIG. 7B illustrates the results of the cyclic voltammetry measurements performed with the first measurement cell of the electrode chip of Example 2.

FIG. 7B illustrates the results of the cyclic voltammetry measurements performed with the first measurement cell of the electrode chip of Example 2.

As illustrated in FIGS. 7A and 7B, the electrode chip of Example 2 could perform an amperometric detection at, for example, −0.4 V, yet there still was room for improvement in configuration. No calibration curve was made.

The electrode chip of Example 2 had the measurement cell-side working electrode surrounded by the driving electrode in the measurement cell as compared with the electrode chip of Example 1. Therefore, the contact between the measurement solution and the electrode was good, rendering it possible to perform electrochemical measurements suitably.

B-2. Electrode Chip of Example 3

An aqueous solution of 0 mM to 0.5 mM of FMA, 0.1 mM of HEPES and 0.1 mM of KCl was added to the first measurement cell of the electrode chip of Example 3. Nothing was added to the other second to sixth measurement cells. An aqueous solution of 2.5 mM of potassium ferrocyanide, 2.5 mM of potassium ferricyanide, 0.1 mM of HEPES, and 3 M of KCl was added to the auxiliary cell. The working electrode WE terminal of the potentiostat was connected to the first measurement cell, and the second to sixth measurement cells were left open.

Cyclic voltammetry measurements were performed under the following conditions: sweep rate: 20 mV/s, electric potential: 0.365 V→−0.3 V→0.5 V→0.365 V, and FMA concentration: 0 mM to 0.5 mM.

Chronoamperometry measurements were performed under the following conditions: applied voltage: −0.2 V, application time: 30 s, and FMA concentration: 0 mM to 0.5 mM.

Figure 8A:
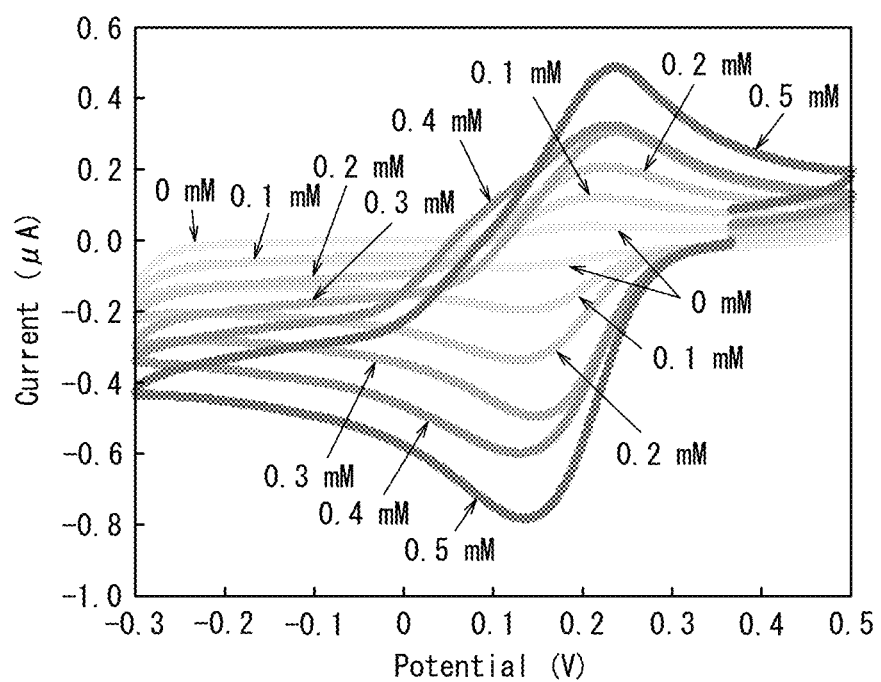
FIGS. 8A and 8B illustrate the evaluation results of the electrochemical measurements performed with the first to sixth measurement cells of the electrode chip of Example 3, with FIG. 8A illustrating the results of the cyclic voltammetry measurements, and FIG. 8B illustrating the results of the chronoamperometry measurements.
Figure 8B:
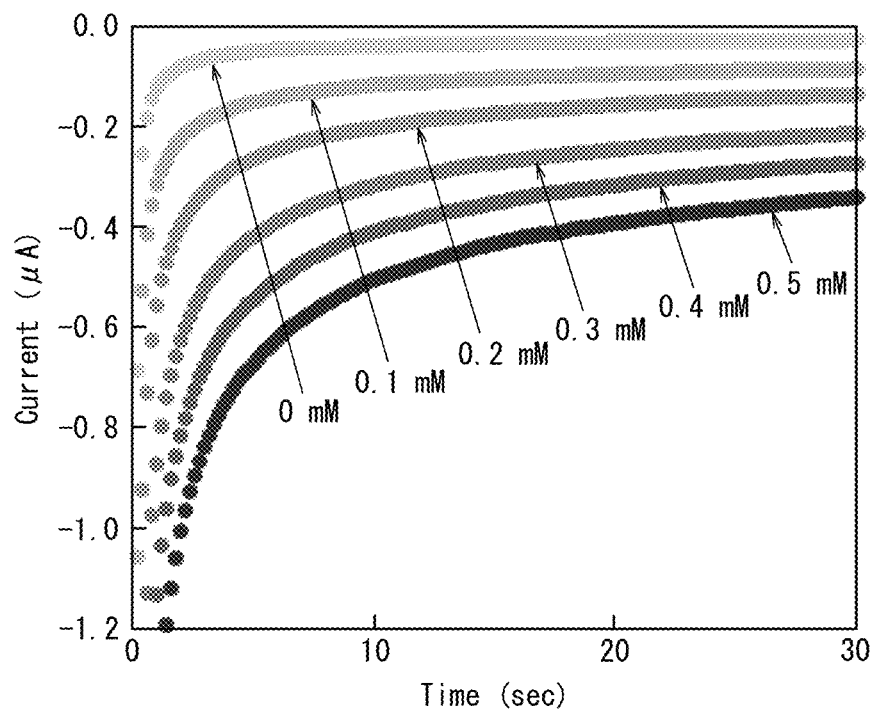

FIGS. 8A and 8B illustrate the evaluation results of the electrochemical measurements performed with the first to sixth measurement cells of the electrode chip of Example 3, with FIG. 8A illustrating the results of the cyclic voltammetry measurements, and FIG. 8B illustrating the results of the chronoamperometry measurements.

Figure 9:
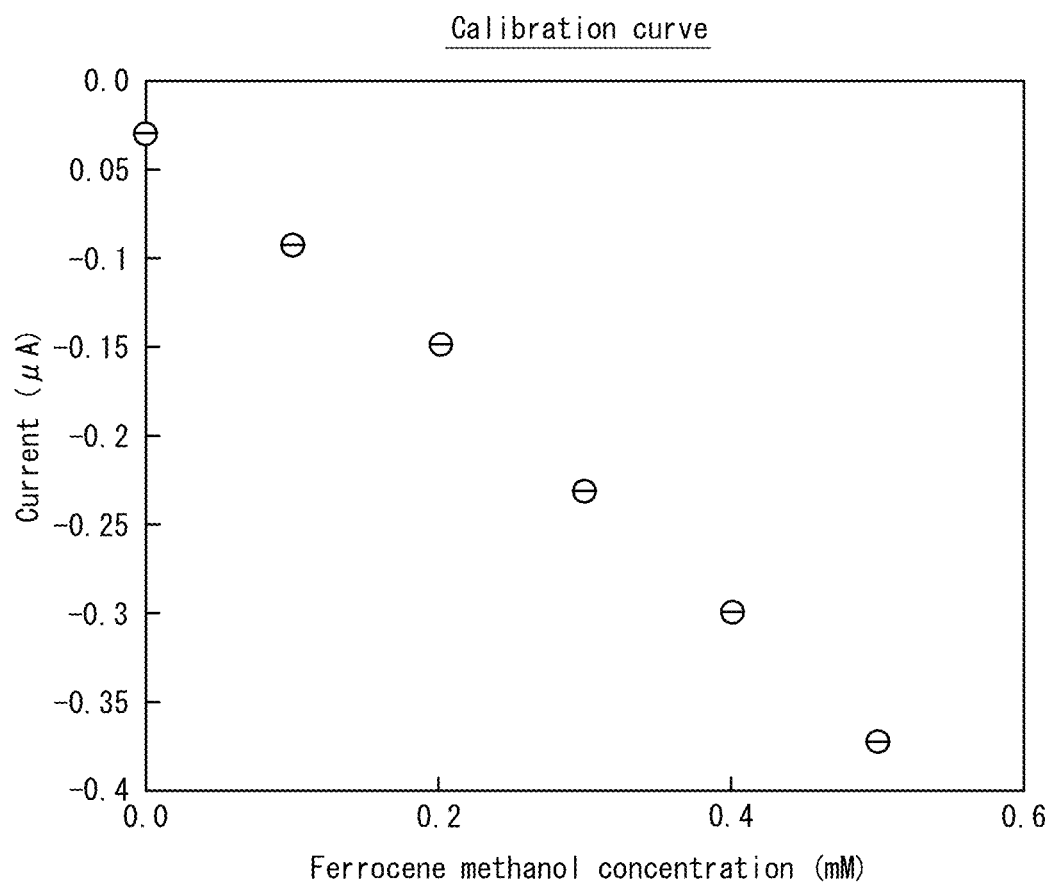
FIG. 9 is a graph plotting the average current value (A) of the chronoamperogram (22 seconds to 25 seconds) against the ferrocene methanol concentration (mM) for the electrode chip of Example 3.

FIG. 9 is a graph plotting the average current value (μA) of the chronoamperogram (22 seconds to 25 seconds) against the ferrocene methanol concentration (mM) for the electrode chip of Example 3.

An aqueous solution of 0.1 mM to 0.5 mM of FMA, 0.1 mM of HEPES and 0.1 mM of KCl was added to the first measurement cell of the electrode chip of Example 3. An aqueous solution of 0.1 mM of FMA, 0.1 mM of HEPES and 0.1 mM of KCl was added to the second measurement cell. An aqueous solution of 0.1 mM of FMA was added to the other third to sixth measurement cells. An aqueous solution of 2.5 mM of potassium ferrocyanide, 2.5 mM of potassium ferricyanide, 0.1 mM of HEPES, and 3 M of KCl was added to the auxiliary cell. The working electrode WE terminal of the potentiostat was sequentially connected to the first and second measurement cells, and the third to sixth measurement cells were left open.

Cyclic voltammetry measurements were performed under the following conditions: sweep rate: 20 mV/s, electric potential: 0.365 V→−0.3 V→0.5 V→0.365 V, and FMA concentration: 0 mM to 0.5 mM.

Figure 10A:
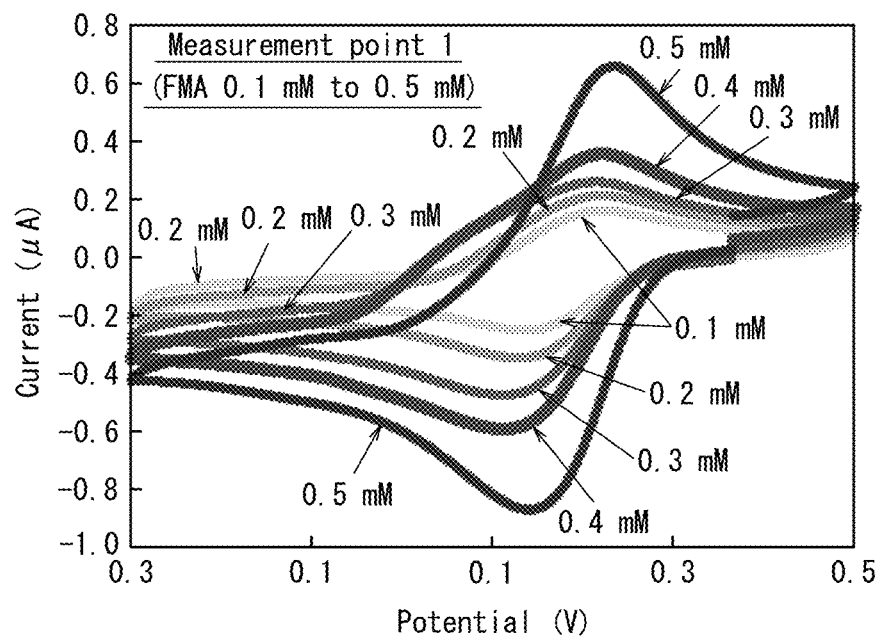
FIG. 10A illustrates the results of the cyclic voltammetry measurements performed with the first measurement cell of the electrode chip of Example 3.
Figure 10B:
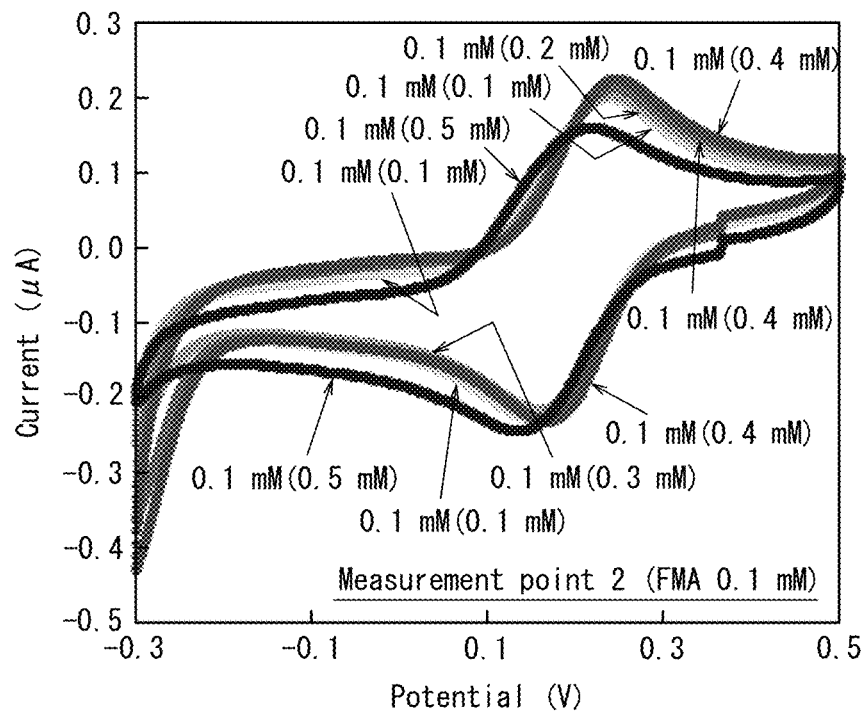
FIG. 10B illustrates the results of the cyclic voltammetry measurements performed with the second measurement cell (the words in the parentheses of the legend of the figure indicate the concentration in the first measurement cell)

FIG. 10A illustrates the results of the cyclic voltammetry measurements performed with the first measurement cell of the electrode chip of Example 3, and FIG. 10B illustrates the results of the cyclic voltammetry measurements performed with the second measurement cell (the words in the parentheses of the legend of the figure indicate the concentration in the first measurement cell).

Chronoamperometry measurements were performed under the following conditions: applied voltage: −0.2 V, application time: 30 s, and FMA concentration: 0 mM to 0.5 mM.

Figure 11A:
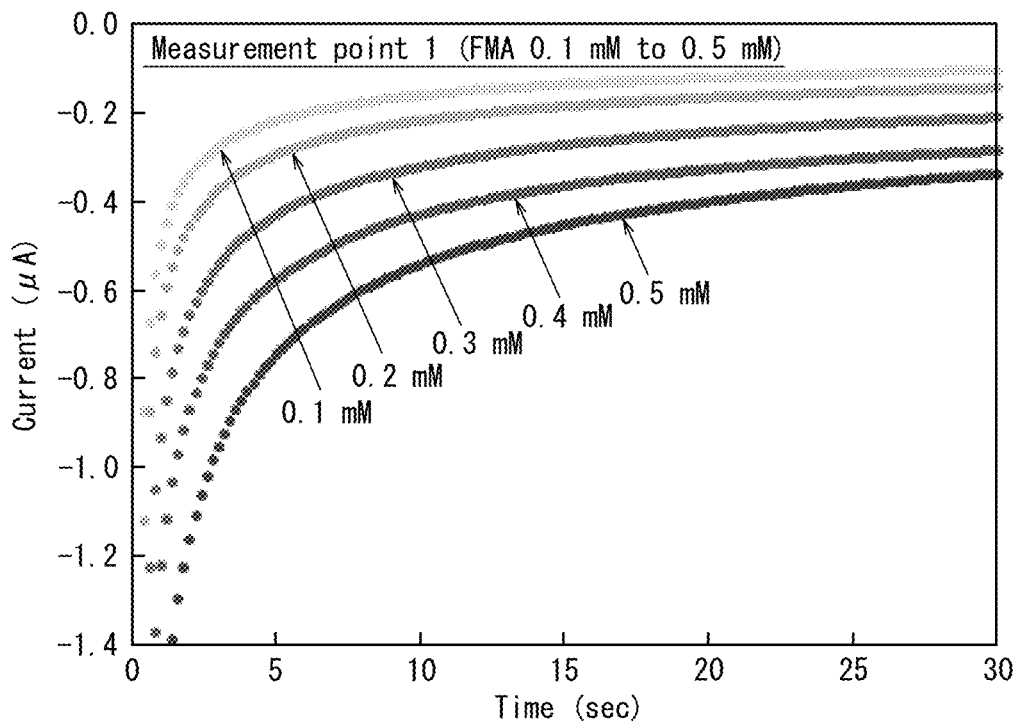
FIG. 11A illustrates the results of the chronoamperometry measurements performed with the first measurement cell of the electrode chip of Example 3.
Figure 11B:
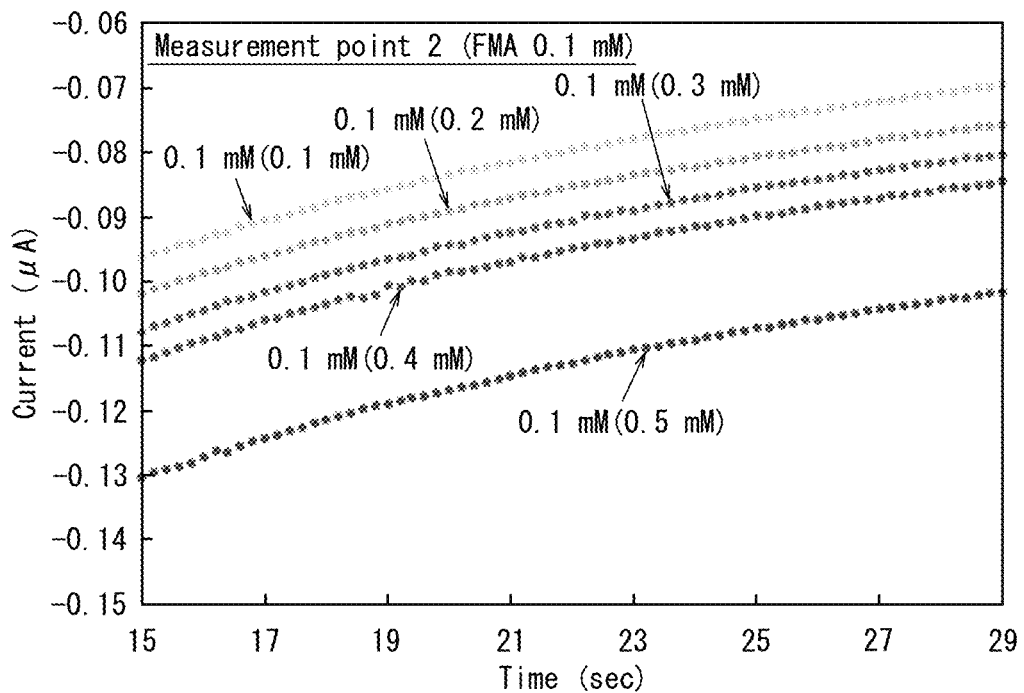
FIG. 11B illustrates the results of the chronoamperometry measurements performed with the second measurement cell (the words in the parentheses of the legend of the figure indicate the concentration in the first measurement cell).

FIG. 11A illustrates the results of the chronoamperometry measurements performed with the first measurement cell of the electrode chip of Example 3, and FIG. 11B illustrates the results of the chronoamperometry measurements performed with the second measurement cell (the words in the parentheses of the legend of the figure indicate the concentration in the first measurement cell).

FIG. 12 is a graph plotting the average current value (A) of the chronoamperogram (22 seconds to 25 seconds) against the ferrocene methanol concentration (mM) for the electrode chip of Example 3.

Although not illustrated in the drawings, it should be noted that in the case of using all the first to sixth measurement cells in Example 3, the time required for measurement with only the first measurement cell was 2 minutes, and the time required for measurement with all the first to sixth measurement cells was 2.5 minutes. It is understood from this fact that the measurement time can be shortened by 9.5 minutes by using the electrode chip of Example 2 as compared with the case of using six conventional electrode chips having only one measurement cell.

An aqueous solution of 0.1 mM to 0.5 mM of FMA, 0.1 mM of HEPES and 0.1 mM of KCl was added to the first measurement cell of the electrode chip of Example 3. An aqueous solution of 0.5 mM of FMA, 0.1 mM of HEPES and 0.1 mM of KCl was added to the second measurement cell. An aqueous solution of 0.5 mM of FMA was added to the other third to sixth measurement cells. An aqueous solution of 2.5 mM of potassium ferrocyanide, 2.5 mM of potassium ferricyanide, 0.1 mM of HEPES, and 3 M of KCl was added to the auxiliary cell. The working electrode WE terminal of the potentiostat was sequentially connected to the first and second measurement cells, and the third to sixth measurement cells were left open.

Cyclic voltammetry measurements were performed under the following conditions: sweep rate: 20 mV/s, electric potential: 0.365 V→−0.3 V→0.5 V→0.365 V, and FMA concentration: 0 mM to 0.5 mM.

Figure 13A:
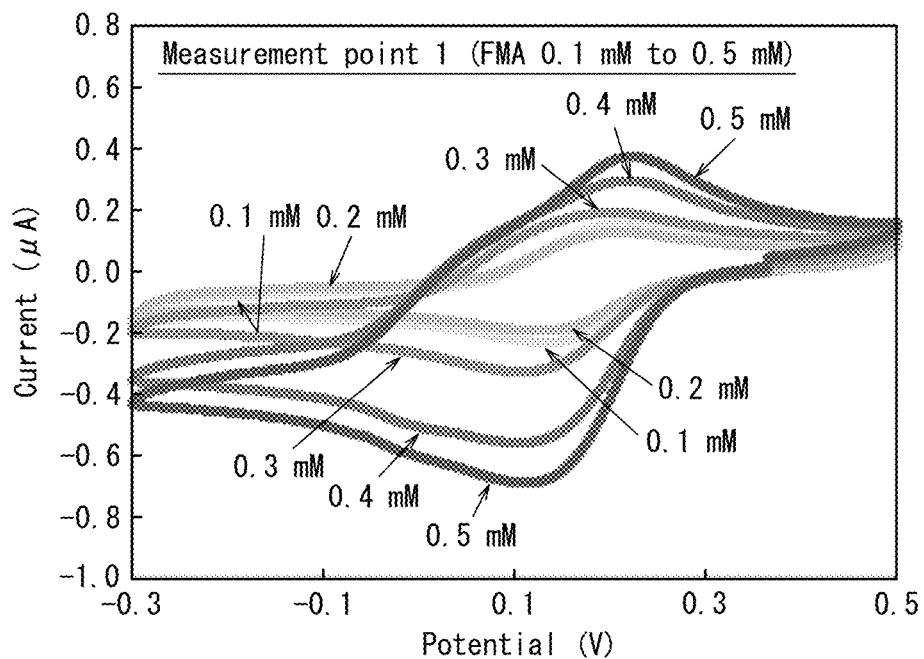
FIG. 13A illustrates the results of the cyclic voltammetry measurements performed with the first measurement cell of the electrode chip of Example 3.
Figure 13B:
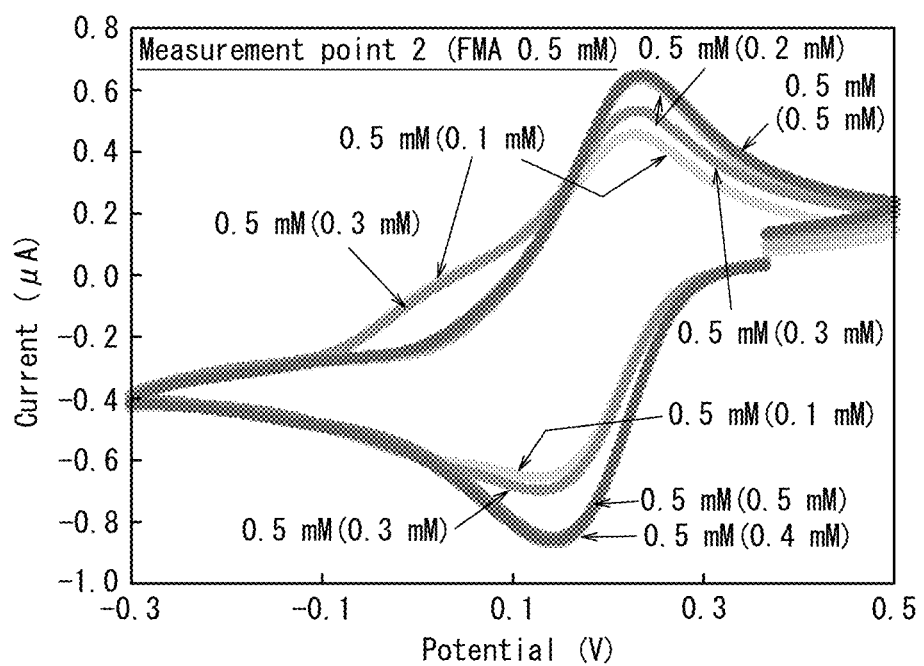
FIG. 13B illustrates the results of the cyclic voltammetry measurements performed with the second measurement cell (the words in the parentheses of the legend of the figure indicate the concentration in the first measurement cell)

FIG. 13A illustrates the results of the cyclic voltammetry measurements performed with the first measurement cell of the electrode chip of Example 3, and FIG. 13B illustrates the results of the cyclic voltammetry measurements performed with the second measurement cell (the words in the parentheses of the legend of the figure indicate the concentration in the first measurement cell).

Chronoamperometry measurements were performed under the following conditions: applied voltage: −0.2 V, application time: 30 s, and FMA concentration: 0 mM to 0.5 mM.

Figure 14A:
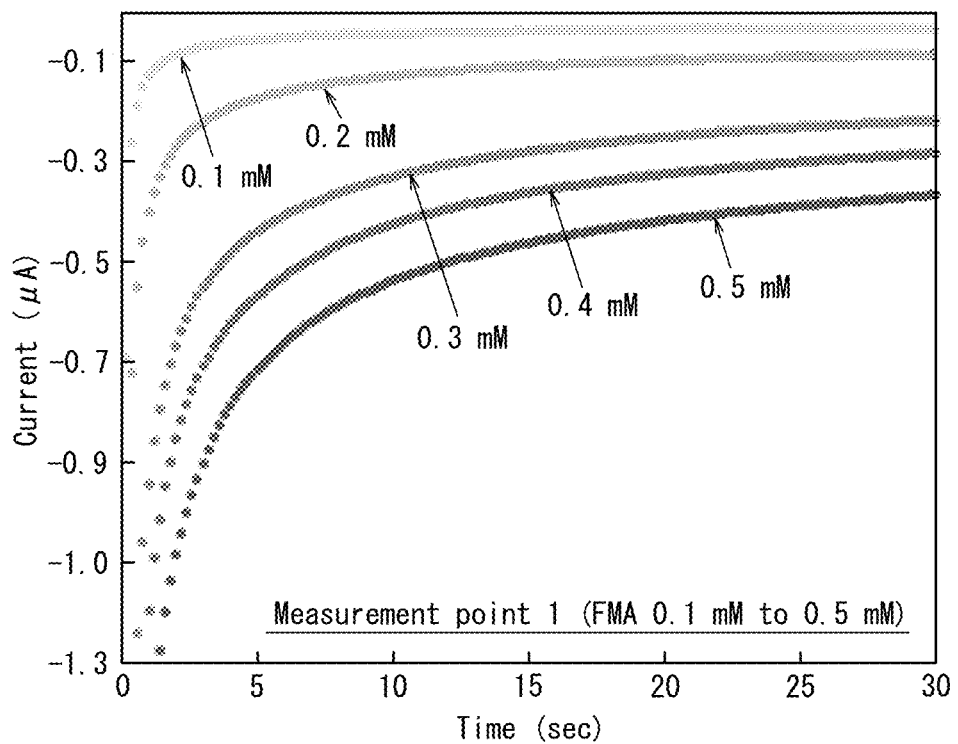
FIG. 14A illustrates the results of the chronoamperometry measurements performed with the first measurement cell of the electrode chip of Example 3.
Figure 14B:
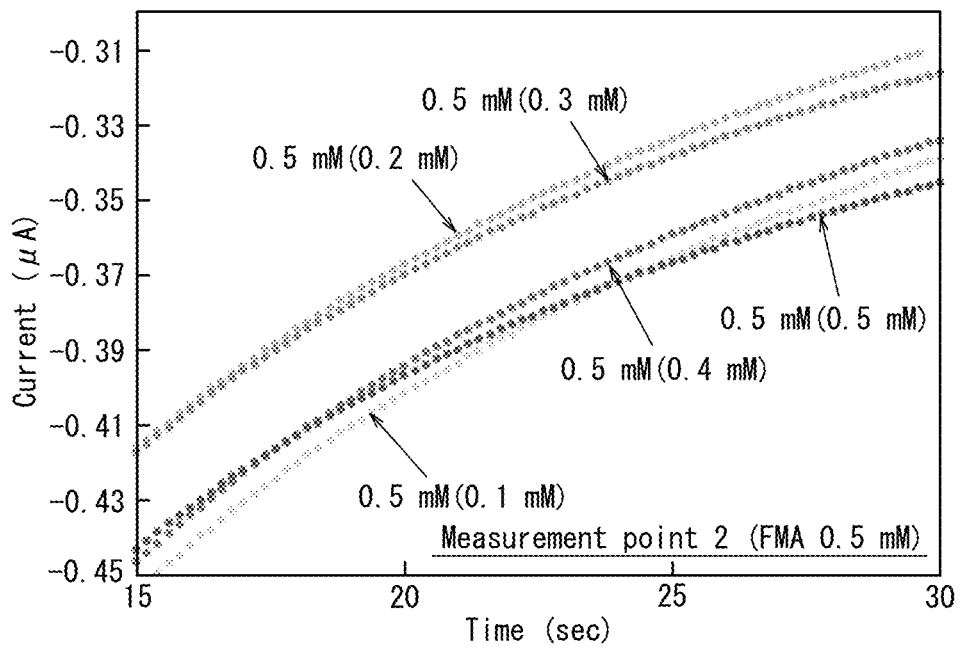
FIG. 14B illustrates the results of the chronoamperometry measurements performed with the second measurement cell (the words in the parentheses of the legend of the figure indicate the concentration in the first measurement cell)

FIG. 14A illustrates the results of the chronoamperometry measurements performed with the first measurement cell of the electrode chip of Example 3, and FIG. 14B illustrates the results of the chronoamperometry measurements performed with the second measurement cell (the words in the parentheses of the legend of the figure indicate the concentration in the first measurement cell).

Figure 15:
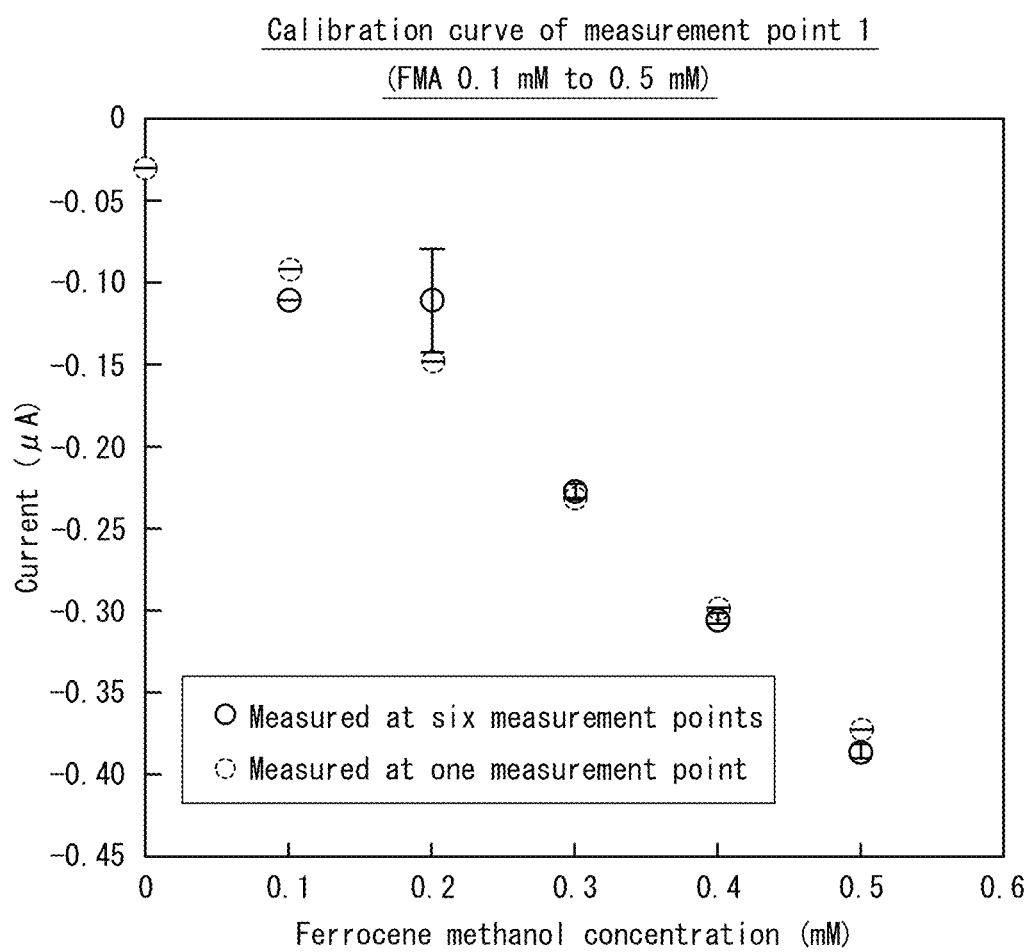
FIG. 15 is a graph plotting the average current value (A) of the chronoamperogram (22 seconds to 25 seconds) against the ferrocene methanol concentration (mM) for the electrode chip of Example 3.

FIG. 15 is a graph plotting the average current value (A) of the chronoamperogram (22 seconds to 25 seconds) against the ferrocene methanol concentration (mM) for the electrode chip of Example 3.

The driving electrode of the electrode chip of Example 3 had a larger surface area as compared with the driving electrode of the electrode chip of Example 2. Therefore, the oxidation-reduction reaction on the measurement cell-side working electrode was the rate-determining reaction of the electrode chip of Example 3, and the electrode chip of Example 3 could perform electrochemical measurements suitably.

INDUSTRIAL APPLICABILITY

According to this disclosure, it is possible to provide an electrode chip that can perform multiple measurements accurately.

The electrode chip of this disclosure can be suitably used, for example, in an immunosensor or a urine sensor.

REFERENCE SIGNS LIST 1 electrode chip
2 substrate
3 auxiliary cell
4 measurement cell
we driving electrode
ce counter electrode
re reference electrode
be bipolar electrode
be3 auxiliary cell-side working electrode
be4 measurement cell-side working electrode
WE working electrode
CE counter electrode
RE reference electrode

The invention claimed is:

1. An electrode chip comprising one auxiliary cell and a plurality of measurement cells on a substrate, wherein
the auxiliary cell comprises a reference electrode, a counter electrode, and an auxiliary cell-side working electrode,
each measurement cell comprises a driving electrode and a measurement cell-side working electrode, and
the auxiliary cell-side working electrode is electrically connected to each measurement cell-side working electrode.

2. The electrode chip according to claim 1, wherein each measurement cell-side working electrode is surrounded by the driving electrode in the measurement cell.

3. The electrode chip according to claim 2, wherein a surface area of the auxiliary cell-side working electrode is larger than surface areas of a plurality of the measurement cell-side working electrodes.

4. The electrode chip according to claim 2, wherein a surface area of the auxiliary cell-side working electrode is larger than a surface area of any one of the measurement cell-side working electrodes.

5. The electrode chip according to claim 2, wherein a surface area of one of the driving electrodes is larger than a surface area of one of the measurement cell-side working electrodes.

6. The electrode chip according to claim 2, wherein a surface area of the counter electrode is larger than a surface area of the auxiliary cell-side working electrode.

7. The electrode chip according to claim 2, wherein a ratio of a surface area of the driving electrode to a surface area of the measurement cell-side working electrode is 2000% to 8000% in each measurement cell.

8. The electrode chip according to claim 1, wherein a surface area of the auxiliary cell-side working electrode is larger than surface areas of a plurality of the measurement cell-side working electrodes.

9. The electrode chip according to claim 8, wherein a surface area of one of the driving electrodes is larger than a surface area of one of the measurement cell-side working electrodes.

10. The electrode chip according to claim 8, wherein a surface area of the counter electrode is larger than a surface area of the auxiliary cell-side working electrode.

11. The electrode chip according to claim 8, wherein a ratio of a surface area of the driving electrode to a surface area of the measurement cell-side working electrode is 2000% to 8000% in each measurement cell.

12. The electrode chip according to claim 1, wherein a surface area of the auxiliary cell-side working electrode is larger than a surface area of any one of the measurement cell-side working electrodes.

13. The electrode chip according to claim 12, wherein a surface area of one of the driving electrodes is larger than a surface area of one of the measurement cell-side working electrodes.

14. The electrode chip according to claim 12, wherein a surface area of the counter electrode is larger than a surface area of the auxiliary cell-side working electrode.

15. The electrode chip according to claim 1, wherein a surface area of one of the driving electrodes is larger than a surface area of one of the measurement cell-side working electrodes.

16. The electrode chip according to claim 15, wherein a surface area of the counter electrode is larger than a surface area of the auxiliary cell-side working electrode.

17. The electrode chip according to claim 1, wherein a surface area of the counter electrode is larger than a surface area of the auxiliary cell-side working electrode.

18. The electrode chip according to claim 1, wherein a ratio of a surface area of the driving electrode to a surface area of the measurement cell-side working electrode is 2000% to 8000% in each measurement cell.

19. The electrode chip according to claim 1, wherein
each measurement cell further comprises a measurement solution containing a detection substance, and the auxiliary cell further comprises an auxiliary solution containing an oxidation-reduction substance, and a ratio of a concentration of the detection substance in each measurement solution to a concentration of the oxidation-reduction substance in the auxiliary solution is 20% or less.

20. The electrode chip according to claim 1, wherein the counter electrode and the reference electrode are electrically insulated and independently provided in the auxiliary cell.

* * * * *